United States Patent [19]
Schulze et al.

[11] Patent Number: 5,673,692
[45] Date of Patent: Oct. 7, 1997

[54] SINGLE SITE, MULTI-VARIABLE PATIENT MONITOR

[75] Inventors: Arthur E. Schulze, Houston; Tommy G. Cooper, Friendswood, both of Tex.

[73] Assignee: BioSignals Ltd. Co., Albuquerque, N. Mex.

[21] Appl. No.: 383,116

[22] Filed: Feb. 3, 1995

[51] Int. Cl.$^6$ .................................................. A61B 5/00
[52] U.S. Cl. .................... 128/633; 128/664; 128/666; 128/736; 356/41
[58] Field of Search .................... 128/670, 664, 128/736, 691, 689, 665, 633, 634, 666

[56] References Cited

U.S. PATENT DOCUMENTS

| | | | |
|---|---|---|---|
| 3,858,574 | 1/1975 | Page | 128/205 |
| 3,910,257 | 10/1975 | Fletcher et al. | 128/670 |
| 4,797,840 | 1/1989 | Fraden | 364/557 |
| 5,109,849 | 5/1992 | Goodman et al. | 128/670 |
| 5,115,133 | 5/1992 | Knudson | 250/341 |
| 5,137,023 | 8/1992 | Mendelson et al. | 128/633 |
| 5,152,296 | 10/1992 | Simons | 128/670 |
| 5,167,235 | 12/1992 | Seacord | 128/664 |
| 5,213,099 | 5/1993 | Fripp, Jr. | 128/633 |
| 5,297,554 | 3/1994 | Glynn et al. | 128/666 |
| 5,361,758 | 11/1994 | Hall et al. | 128/633 |
| 5,469,855 | 11/1995 | Pompei et al. | 128/664 |
| 5,509,422 | 4/1996 | Fukami | 128/670 |

FOREIGN PATENT DOCUMENTS

| | | |
|---|---|---|
| 2653959A1 | 6/1978 | Germany . |
| 3910749A1 | 4/1989 | Germany . |

OTHER PUBLICATIONS

T. Shinozaki, MD, et al, "Infrared Tympanic Thermometer: Evaluation of A New Clinical Thermometer", *Critical Care Medicine*, 1988, vol. 16, No. 2., pp. 148–150.

R. C. Cork, MD PhD, et al, "Precision And Accuracy of Intraoperative Temperature Monitoring", *ANESTH ANAGL*, 1983, vol. 62, pp. 211–214.

J. J. Nobel, MD, "Infrared Ear Thermonetry", *Pediatric Emergency Care*, Feb. 1992, vol. 8, No. 1, pp. 54–58.

J. Vandeput, MD, et al "Photoelectric Plethysmography In Monitoring Skin Circulation", *Southern Medical Journal*, May 1990, vol. 83, No. 5, pp. 533–537.

Y. Mendelson, PhD, et al, "Noninvasive Measurement Of Arterial Oxyhemoglobin Saturation With A Heated And A Non–heated Skin Reflectance Pulse Oximeter Sensor", *Biomedical Instrumentation & Technology*, Nov./Dec. 1991, pp. 472–480.

S. Schotz, MD, et al, "The Ear Oximeter As A Circulatory Monitor", *Anesthesiology*, May–Jun. 1958, vol. 19, No. 3, pp. 386–393.

*Primary Examiner*—Robert Nasser
*Attorney, Agent, or Firm*—Norman E. Brunell

[57] ABSTRACT

An apparatus for monitoring multiple physiological variables of a patient at a single site on the patient can be used to facilitate assessment of the patient's well being during medical surgery as well as during ambulatory monitoring, home monitoring, procedure monitoring and similar situations. The apparatus has an infrared (IR) temperature sensor, a pulse oximeter sensor and a communication circuit for outputting information produced from the pulse oximeter and information produced from the infrared temperature measuring device. These elements are integrally placed within a mold or plug made to fit the ear of the patient.

8 Claims, 6 Drawing Sheets

SINGLE SITE, MULTI-VARIABLE PATIENT MONITOR

TECHNICAL FIELD OF THE INVENTION

The present invention is related in general to monitoring physiological variables of a patient and in particular to a device for remotely monitoring multiple physiological variables from a single site on the body of a patient.

BACKGROUND OF THE INVENTION

Continuous monitoring of physiological variables, such as body core temperature, is important in patient care, particularly during surgery. However, presently known methods of continuously monitoring physiological variables have been found to be quite unsatisfactory.

For example, methods such as monitoring a patient's temperature through rectal probes or by inserting a thermistor or thermocouple against a tympanic membrane/ear canal are not well liked by either patients or care givers.

On the other hand, less intrusive methods such as monitoring body temperature through skin measurements can only provide rough indicators of changes in the temperature of a patient. Furthermore, rather than measuring body core temperature directly, these methods can only provide a rough approximation thereof. Moreover, skin temperature measurements are susceptible to environmental changes such as body movement and changes in surrounding temperature, light, air currents, and the like.

SUMMARY OF THE INVENTION

The present invention provides, in a first aspect, apparatus for monitoring multiple physiological variables of a patient at a single site on the body of the patient.

In one aspect, the present invention provides a single probe with an infrared (IR) temperature sensor, a pulse oximeter sensor, and a communication circuit for outputting information generated by the pulse oximeter sensor and the IR temperature sensor.

In another aspect, the present invention provides a monitoring system having at least two sensors for measuring different physiological variables of a patient in the ear canal of the patient including measurements of the ear canal itself as well as measurements of the tympanic membrane, a communication circuit coupled to the sensors for communicating outputs of the sensors to an external processor, a battery for supplying power to the sensors and the communication circuit, and a support for coupling the apparatus to the ear canal. The monitoring system also includes an external processor receiving outputs of the sensors from the communication circuit for processing the outputs of the sensors into physiological data.

In still another aspect, the present invention provides a method for monitoring multiple physiological variables of a patient. The method includes the steps of measuring at least two different physiological variables of the patient from the ear canal by coupling at least two sensors to the tympanic membrane and ear canal, communicating outputs of the sensors to an external processor, and processing the outputs of the sensors at the external processor into physiological data.

In still another aspect, the present invention provides a method for monitoring multiple physiological variables of a patient. The method includes the steps of measuring at least two different physiological variables of the patient from an ear by coupling at least two sensors to the ear, communicating outputs of the sensors to an external processor, and processing the outputs of the sensors at the external processor into physiological data.

In yet another aspect, the present invention provides an apparatus for monitoring multiple physiological variables of a patient, including a housing to fit in the ear canal of a patient. The housing has an inner end, an outer end, an elongated hollow section between the ends, and a pair of openings through the wall of the hollow section. One or more radiation sources is mounted along one of the openings to emit radiation toward the lining of the ear canal of the patient; and a radiation sensor is mounted along the other opening to receive radiation from the source following reflection and or conduction by the lining of the ear canal. An additional radiation sensor is also mounted on the housing to receive radiation from the tympanic membrane of the patient.

A substrate, which carries the radiation sources, is disposed along the housing opening for the source. Similarly, another substrate, which carries the companion radiation sensor to the radiation source, is disposed along the housing opening for that sensor.

DETAILED DESCRIPTION

Figures 1, 4:
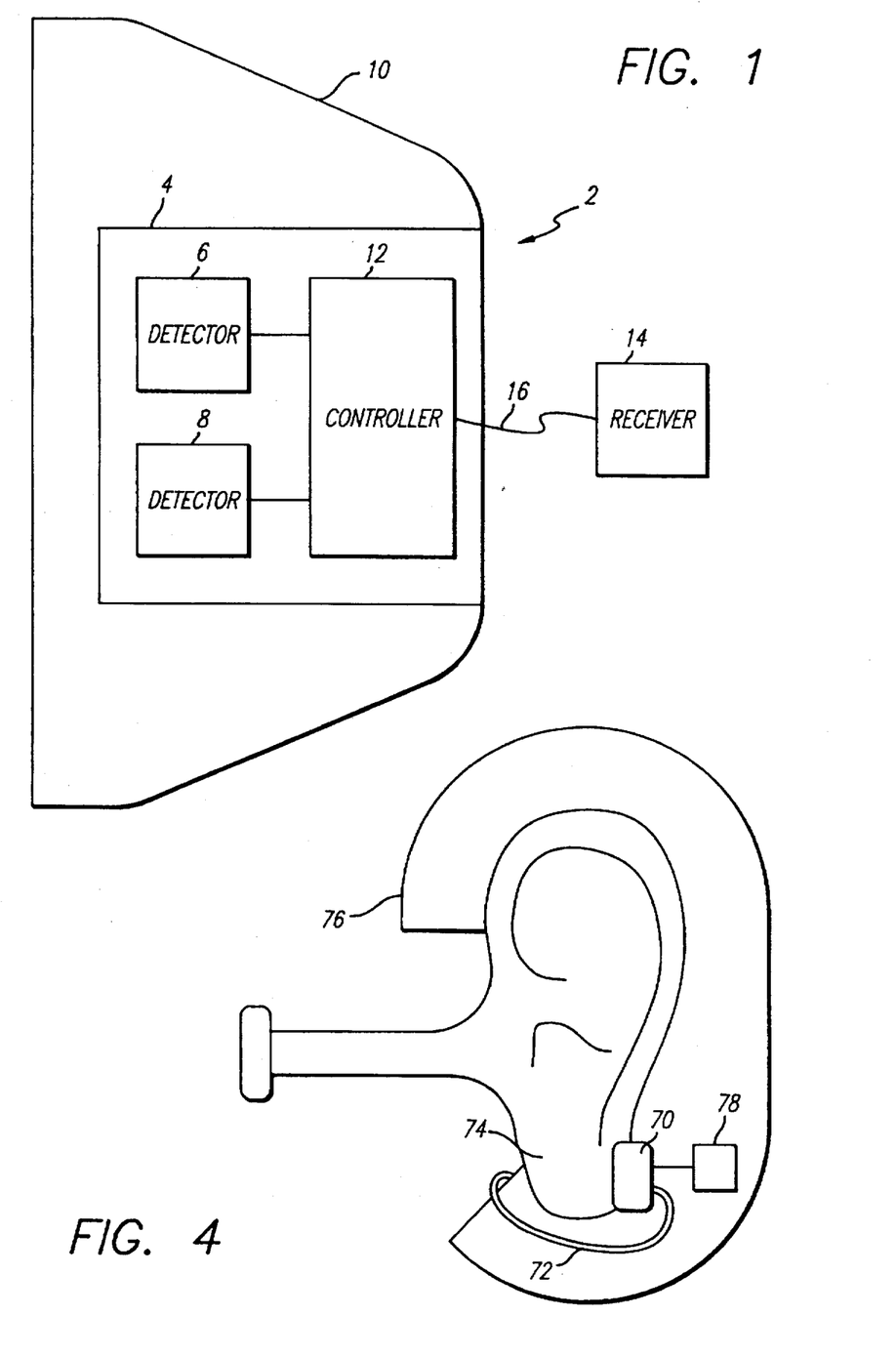
FIG. 1 is a block diagram depicting a system for monitoring multiple physiological variables at a single site on the body of a patient.
FIG. 4 depicts a monitoring system where the sensors are clamped to an ear by a clip.

FIG. 1 is a block diagram of a system 2 for monitoring multiple physiological variables of a patient at a single site on the body of the patient, preferably the ear. The system 2 has an apparatus 4 having at least a first sensor 6 and a second sensor 8 affixed to a support 10, such as an ear muff or a plug, for holding the first and second sensors 6 and 8 at one ear of the patient.

Each of the first and second sensors 6 and 8 measures one or more physiological variables of the patient under control of a controller 12. Controller 12 also operates to preprocess the output signals from the sensors 6 and 8 into data which is communicated to a receiver 14. The receiver 14 can be a human operator. The receiver 14 can also be an external processor which further processes the data into required physiological information.

Communication can be performed by either wireless transmission (e.g., by infrared signals or by radio frequency signals) or by wired transmission (e.g., multi-channel cable, fiber optic medium or multiplexed transmission).

Figure 2:
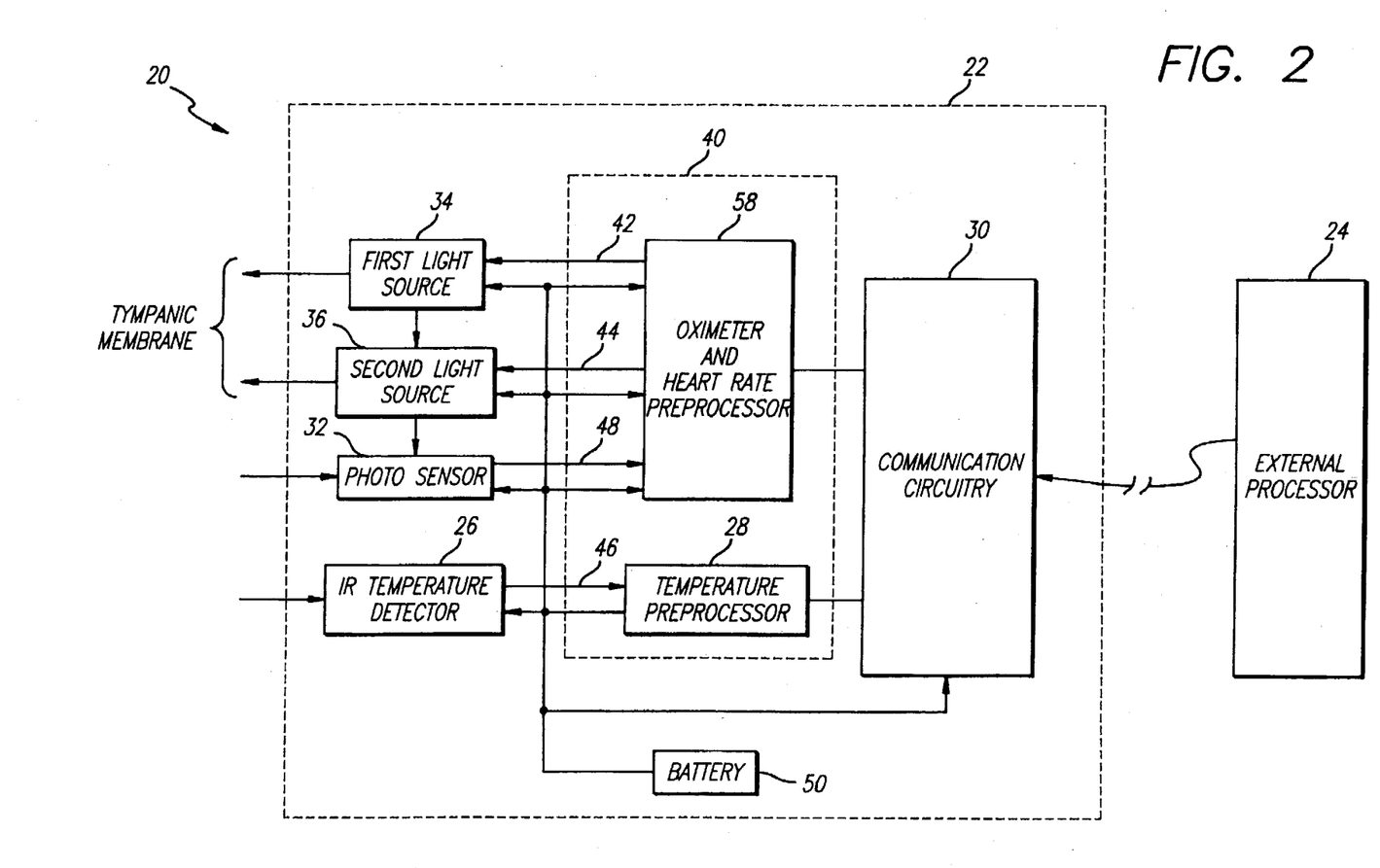
FIG. 2 is a block diagram of a system whereby physiological variables including core temperature, heart rate and oxygen saturation monitored at a single site on the body of a patient.

FIG. 2 is a block diagram depicting a monitor system 20 wherein the present invention is embodied. The monitor system 20 has a circuit 22 which operates to measure physiological variables of a patient. The monitor system 20 also has an external processor 24 which operates to process data obtained by the circuit 22.

In operation, circuit 22 is coupled to a site on the body of the patient. The ear is chosen as such a site because the tympanic membrane provides a reliable indication of the patient's body core temperature. The lack of pigmentation in the tympanic membrane also makes calibration factors more constant across age and race of the patients. Moreover, the ear can be accessed more conveniently during most routine medical procedures, including surgery. The ear is also thermally isolated from room environment, and is largely insensitive to vasoconstriction and vasodilation because arterial flow through the carotid artery, which supplies blood to the tympanic membrane, is usually maintained even during shock.

Circuit 22 has an infrared (IR) temperature sensor 26 for measuring body core temperature of the patient. A thermistor may also be used as temperature sensor 26 if positioned in contact with the body. IR temperature sensor 26 is aimed at the tympanic membrane and outputs a signal in response to the temperature of the tympanic membrane. The output signal is sent to an IR temperature preprocessor 28, which has amplifiers and compensation devices for conditioning the signal for transmission.

The output of preprocessor 28 is then communicated to the external processor 24 for further processing. Using the external processor 24 to further process the data ensures that there is minimal loss of data through preprocessing and that data processing algorithms are not restricted by the lack of electrical power to the sensors and or a lack of space in the support.

Communication between the circuit 22 and the external processor 24 is performed by a communication circuit 30, such as a radio frequency transmitter or an infrared transmitter. Communication between the circuit 22 and the external processor 24 can also be performed through a multi-channel cable, a fiber optic channel or multiplexed cable transmission, and/or through a local area network (LAN).

In one embodiment of the present invention, communication between the circuit 22 and the external processor 24 is unidirectional and includes only data from the circuit 22 to the external processor 24. In an enhanced embodiment, communication between the circuit 22 and the external processor 24 is bi-directional and includes data sent from the circuit 22 to the external processor 24, as well as control signals sent from the external processor 24 to the circuit 22 to selectively set such parameters as the rate of sampling and/or the gains of the circuit 22.

Circuit 22 also has a pulse oximetry sensor (POS) for measuring oxygen saturation and heart rate of the patient. The POS includes a first radiation source 34 such as a light emitting diode (LED), a second radiation source 36 and a photosensor 32, each of which operates under the control of a POS preprocessor 38.

Figure 3:
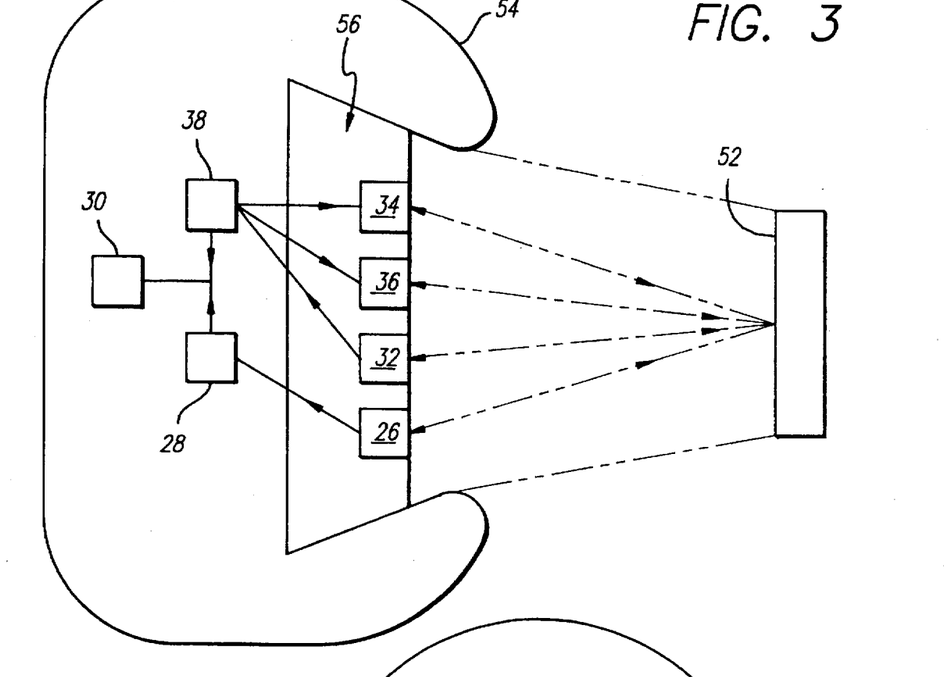
FIG. 3 depicts how the core temperature, heart rate and oxygen saturation are monitored from the ear by the system shown in FIG. 2.

With reference to FIG. 3, the IR temperature sensor 26, the first and second radiation sources 34 and 36, and the photosensor 32 can be placed in a plug 56 for insertion into the auditory canal, and aimed at the tympanic membrane 52 but without touching it. The preprocessors 28 and 38 and the communication circuit 30 can be placed outside of the plug 56 and supported by an ear muff 54.

In other implementations, the first and second radiation sources 34 and 36 can be aimed at the tissue lining the ear canal. They can be placed outside of the auditory canal. The optical radiation from the first and second radiation sources 34 and 36 can be directed by optical fibers into the auditory ear canal and aimed at the tympanic membrane 52. Under such implementation, the first and second radiation sources 34 and 36, along with other components of the circuit 22, can be supported by an ear muff.

Pulse oximetry data is obtained using a conventional technique by having the first and second radiation sources 34 and 36 projecting optical radiation with different wavelengths to the inner surface of the auditory canal or the tympanic membrane 52. The POS preprocessor 38 operates to activate and deactivate the first and second radiation sources 34 and 36 repetitively at a predetermined frequency (say, 75 Hz). Optical radiation from the first and second radiation sources 34 and 36 is absorbed by hemoglobin and oxygen-enriched hemoglobin differently depending on the wavelengths of the optical radiation. Optical radiation reflected by the tissue in the lining of the canal or tympanic membrane 52 is detected by the photosensor 32. The photosensor 32 converts the reflected optical radiation into electrical signals which are sent to the POS preprocessor 38. The POS preprocessor 38 processes the signals 32 into a form acceptable to the communication circuit 30. The communication circuit 30 communicates the digital data to the external processor 24 for further processing.

The external processor 24 can be programmed to convert the output from the circuit 22 to provide oxygen saturation of the arterial blood, based upon the difference in absorption of optical radiation by hemoglobin and oxygen-enriched hemoglobin at different wavelengths.

The external processor 24 can also be programmed to convert the output for the circuit 22 to provide heart rate information of the patient. Heart rate is determined from changes in blood volume caused by pulsatile blood flow associated with the arterial pulse. The changes in the blood volume affect the amount of optical radiation transmitted through the tympanic membrane 52 and the amount of optical radiation reflected from the tympanic membrane 52. Heart rate can then be computed by measuring the time between peaks of the electrical signal generated by the photosensor 32.

The external processor 24 can be optionally programmed to measure respiration rate of a patient. Regular respiration can usually be recognized by small cyclical variations in heart rate (or in the amplitude of an electrocardiogram). Respiration rate is especially measurable under this method in those patients, such as artificially ventilated patients (e.g., those undergoing anesthesia), or patients with pronounced sinus arrhythmia for whom respiration rate is reflected by variations in the beat-to-beat rhythm of the heart. Algorithms, such as logarithmic amplification of the measured data, can be implemented in the external processor 24 to facilitate measurement of respiration rate and to increase the population of patients for whom respiration rate can be measured by this technique.

The IR temperature sensor 26, the first and second radiation sources 34 and 36 may be aimed away from the tympanic membrane to prevent thermal interference with the IR temperature sensor 26 during long term monitoring.

Thermal interference can also be reduced by measuring the output from the IR temperature sensor 26 during a period when the radiation sources 34 and 36 are turned off in a time-division multiplex manner.

Although the temperature preprocessor 28 and the POS preprocessor 38 are shown as separate blocks in FIG. 2, they might actually be different software functions executed by a single microprocessor 40. In the preferred embodiment, the first and second radiation sources 34 and 36 are coupled to respective ones of output ports 42, 44 of the microprocessor 40, and the IR temperature sensor 26 and the photosensor 32 are coupled to respective ones of two input ports 46, 48 of the microprocessor 40.

With regard to the use of signals relating two different wavelengths to determine oxygen saturation, the technique is well known and understood by those familiar with the field of art. The technique is based on the recognition that the difference in signals related to the absorption and/or reflection of light at two different wavelengths can be used to determine the proportion of oxygen carrying hemoglobin in the blood. Similarly, the variations in such signals can be used to monitor pulse rate and/or respiration rate in accordance with conventional techniques.

Operation of the circuit 22 is powered by a battery 50 in the preferred implementation because of the power required by the circuit 22.

Various modifications and substitutions can be made without departing from the scope of the invention.

For example, the IR temperature sensor 26 can be placed so that it touches the tissue of the ear canal and is aimed at or near the tympanic membrane 52. The ear plug 56 is designed to provide sufficient thermal insulation such that insertion of the IR temperature sensor 26 does not cool the tissue being measured or even when the tissue is cooled by direct contact, a thermal equilibrium is re-established over a short period of time as the sensor 26 remains in place.

With reference to FIG. 4, pulse oximetry can also be measured by an optical sensor 70. The optical sensor 70 can be held in place by a clip 72 clamped to the ear lobe 74. An ear muff 76 can be used to support other components 78, such as the preprocessor and the communication circuit. There are sources located on the other side of the ear lobe so that the sensor can sense absorption of the optical signal by the ear lobe.

Heart rate can also be measured from the tissues of the ear using optical plethysmography techniques which detect instantaneous changes in the volume of the blood in the tissue. The detection is performed by projecting an optical radiation to the tissue of the ear and measuring changes in opacity or reflectance resulting from changes in the volume of blood in the tissue.

In other implementations, heart rate can also be monitored from the tissues of the ear canal using either pulse oximetry or optical plethysmography techniques.

Figure 5:
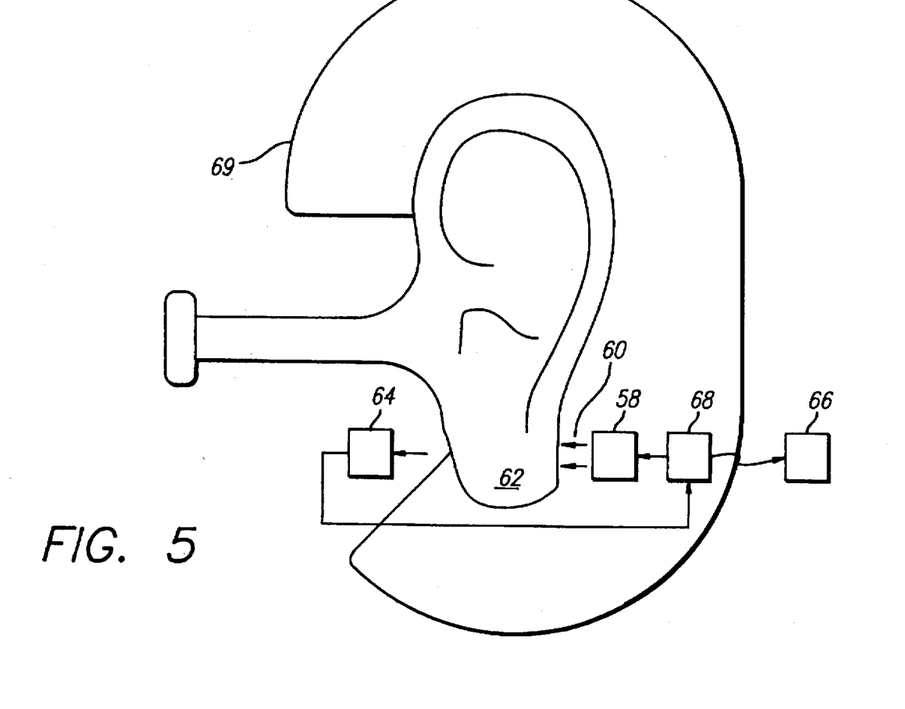
FIG. 5 depicts a monitoring system wherein physiological variables are measured by measuring optical radiation transmitted through an ear lobe.

In other implementations, heart rate can also be monitored from the ear lobe or concha. With reference to FIG. 5, one or more light sources 58 can be provided to project optical radiation 60 to the external tissues of the ear 62 from one side of the ear. The optical radiation transmitted through the ear lobe 62 is measured by one or more photosensors 64 placed on the other side of the ear. Measurements of the optical radiation transmitted through the ear lobe 62 are sent to an external processor 66 through a preprocessor 68. The external processor 66 processes data from the photosensor or photosensors 64 using conventional pulse oximetry techniques to determine the heart rate. In such implementation, the light source or sources 58, photosensor or photosensors 64 and processor 66 can be supported by an ear muff 69 placed at the patient's ear.

While the above shows how heart rate is measured by detecting optical radiation transmitted through the ear lobe, heart rate can also be monitored by measuring optical radiation reflected from the ear lobe or concha (including, e.g., use of pulse oximetry radiation).

Heart rate can also be monitored from the ear lobe or concha through the use of light sources, sensors, and data processing of optical plethysmography (e.g., through transmission or reflection measurements).

Bio-potentials associated with the cardiac cycle and transducable at the surface of the skin (i.e., electro-cardiogram or ECG) can be measured at numerous sites on the body. Heart rate can therefore be monitored by applying two electrodes at any two locations on or near the ear and measuring the ECG bio-potential between the two locations. Similarly, heart rate can be monitored from any two locations on or near the ear using known impedance plethysmography techniques.

In accordance with such techniques, a constant amplitude electrical current is applied between two terminals placed respectively at the two locations. The electrical potential measured across the two terminals as a result of the applied electrical current is detected. This electrical potential is directly proportional to the impedance of the tissue. Since electrical conductivity changes when the amount of blood passing through the ear changes in response to the heart beat, by measuring changes in the electrical potential across the two terminals, variations in the amount of blood passing through the ear, and therefore the heart rate, can be measured.

In accordance with the Raman Effect, the frequency and/or phase of electromagnetic radiation are changed when passing through a transparent medium. Oxygen saturation of arterial blood can therefore be measured from the ear lobule, concha, antihelix, helix, triangular fossa, tragus or antitragus by projecting, through fiber optics, an optical radiation through the semi-transparent tissue.

The present invention can also be used to measure gases, glucose, lactate, and other organic compounds in blood through non-invasive spectroscopic means.

Alternative sites on the ear can also serve as sites for placement of electrodes for the measurement of electrocardiograms, electroencephalograms, electromyograms, and event-related potentials. However, in the measurement of bio-potentials, it is sometimes necessary to locate another (second) electrode and, perhaps, telemetry transmitter at another site on the body in order to obtain a potential difference with a usable vector.

The support for the circuitry can be an ear mold which is custom-made to fit the ear of a patient such that the sensors are located in a way to ensure the transduction of a signal from the tympanic membrane. On the other hand, the support can also have a standardized shape and/or size, or have an adjustable shape and/or size so that a monitoring device can be available to any patient during emergency. The support can be made with either disposable or non-disposable material.

Figures 10, 11, 13:
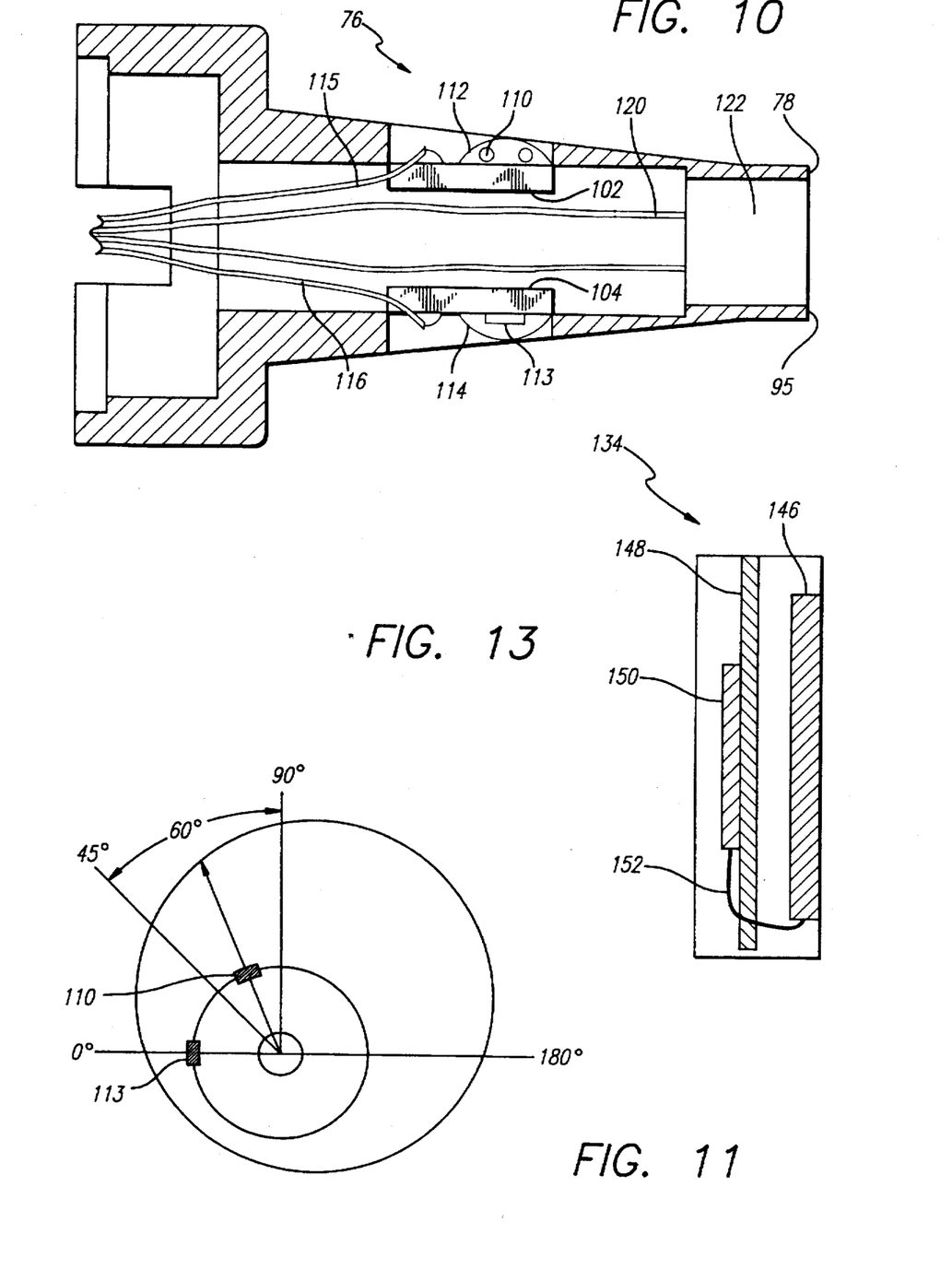
FIG. 10 is the same view as FIG. 9 but with the sources, sensor and detector mounted in the housing.
FIG. 11 is a top planar view of housing 76 illustrating the range of angular separations for radiation sources 110 and radiation detector 113.
FIG. 13 is a cross sectional view and enlargement of transmitter package 134 shown in FIG. 12.

FIGS. 6 through 10 show a housing for sources, a sensor and a detector such as those represented in FIG. 2, but with the sources and sensor using the ear canal lining, while the detector uses the tympanic membrane. FIG. 10 shows the housing, in the same view as FIG. 9, but with the sources, sensor and detector mounted in the housing.

The housing 76 can be made of any suitable material for insertion into the ear canal. Plastic-type materials which are readily molded, such as polyamide or nylon materials, are convenient and efficient examples. The housing has an inner end 78, to be positioned in the ear canal, and an outer end 80.

Starting at the inner end 78, there is an elongated section 82 of the housing having a generally tapered outside wall 84, which is tapered outwardly (from the axis 83 of the housing) toward the outer end 80. This taper exists along the elongated section except for a short distance in proximity to the inner end 78.

Toward the outer end, there is a plug section 86 of the housing. In position, an inner wall surface 90 of this plug section, which faces toward the inner end 78 of the housing, fits adjacent the outer ear.

The housing is hollow in that it has an elongated section opening 90 through the elongated section 84 of the housing, leading to a plug section opening 94 through the plug section 86 of the housing. The elongated section opening then opens at the inner end 78 of the housing, providing an inner end entrance opening 95 at that point, and the plug section opening similarly opens at the outer end 80.

Along the elongated section 82 of the housing, there is also a pair of mounting openings through the wall of the section. In the view of FIGS. 6 through 10, there is a top mounting opening 94 and a bottom mounting opening 96. Such openings are shown to be positioned 180 degrees apart from one another along the elongated section 82 of the housing, but are otherwise essentially identical.

As shown in FIG. 11, the openings and the transducers mounted therein need not be positioned only at 180° apart as depicted in FIGS. 6–10 but may preferably also be positioned in a range of about 45° to 90° apart. In particular, as depicted in FIG. 11, the preferred angular separation of the transducers is about 60° apart. The angular separation of these openings and transducers significantly effects the signal to noise ratio of the signals detected. These detected signals include both skin reflectance factors as well as skin conductance factors. The actual angular separation used may well depend on the particular transducers used as well as their operating wavelengths.

Figure 6:
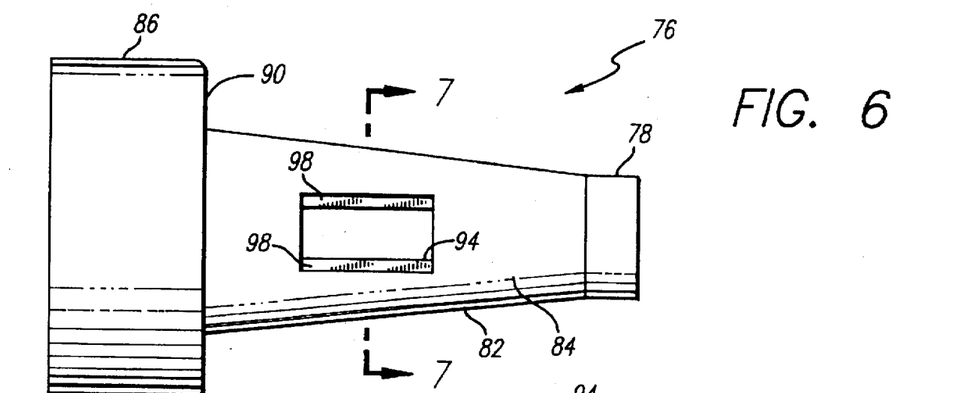
FIG. 6 is a top plan view of a housing for sources, a sensor and a detector such as those represented in FIG. 2, but with the sources and sensor using the ear canal lining, while the detector uses the tympanic membrane.
Figures 7, 8, 9:
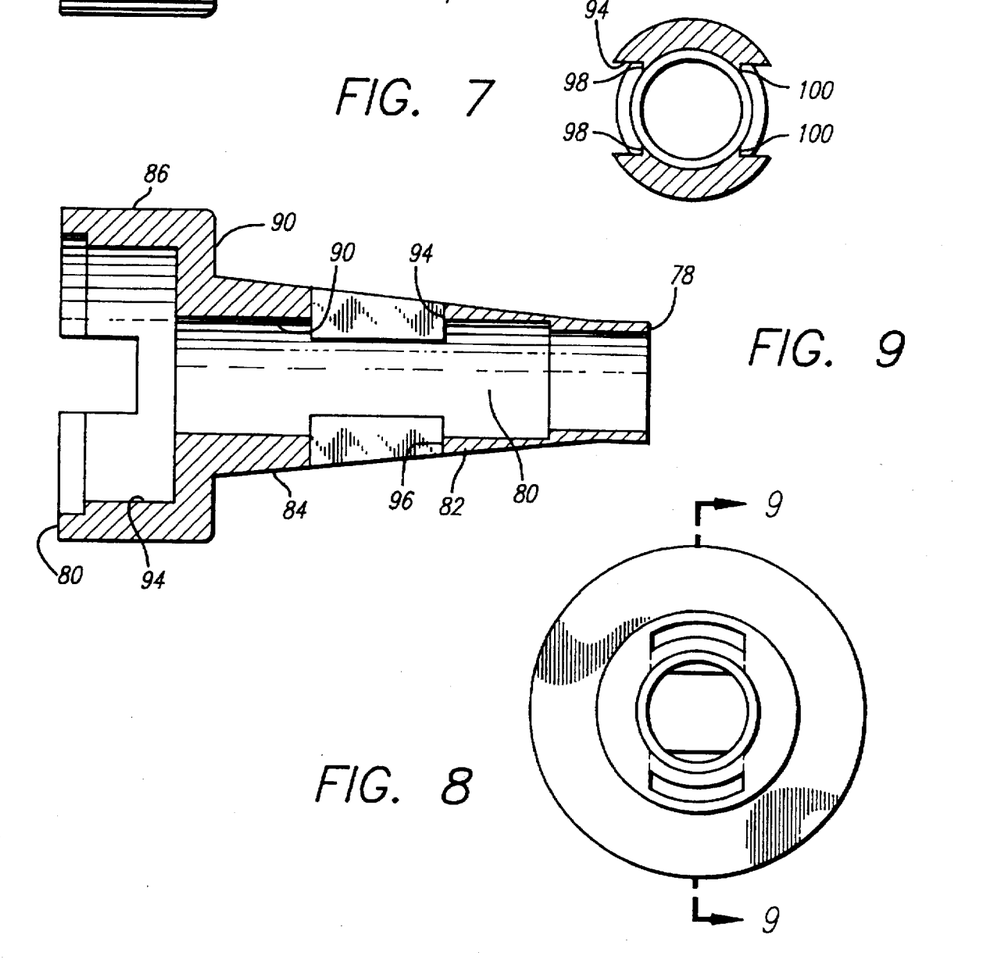
FIG. 7 is a cross-sectional view taken along the line 7—7 of FIG. 6.
FIG. 8 is an end view of the housing of FIG. 6
FIG. 9 is a cross-sectional view taken along the line 9—9 of FIG. 8.

As shown in FIGS. 6 and 7, when each mounting opening is formed, a pair of side ledges is left for mounting purposes. Thus, there is an elongated pair of side ledges 98 at the top opening and an elongated pair of side edges 100 at the bottom opening.

In FIG. 10, a top opening substrate 102 is mounted on and adhered to the elongated side ledges 98 of the top opening and a bottom opening substrate 104 is similarly mounted on and adhered to the elongated side ledges of the bottom opening. The top opening substrate carries a pair of pulse oximetry radiation sources 110 mounted on the substrate, surrounded by a bubble 112 of an appropriate mounting material such as an epoxy material. In accordance with conventional pulse oximetry techniques as referenced herein, the radiation from the sources is at two different wavelengths. In position in the ear, such radiation then is transmitted toward the ear canal lining and reflects off such lining.

On the bottom opening substrate 104, there is similarly mounted a pulse oximetry sensor or detector 113 to detect radiation originating from the sources, at a point after reflection and/or conduction from the ear lining wall, for pulse oximetry purposes. This sensor is also similarly surrounded by a dome shaped cover 114 of an appropriate mounting material, such as an epoxy material. As previously explained, the pulse oximetry signals, of course, can also be used to determine the heart rate of the patient. As previously indicated, the sources and detectors are appropriately connected in the apparatus shown in FIG. 2 with, however, the sources directed at the ear wall lining rather than the tympanic membrane.

The substrates 102 and 104 can conveniently and efficiently be made of conventional materials for mounting electronic parts, such as conventional fiberglass or ceramic circuit board material. Lines of conductive material (not shown) are used to connect leads from the sources 110 and detector 113 to parts of the apparatus outside the housing. In FIG. 10, a single upper lead 115 to the top substrate and a single lower lead 116 to the bottom substrate are shown for purposes of illustration. There would, however, typically be two leads for each of the referenced source and sensor components, although there could be variations in accordance with conventional electrical connection techniques. Rather than extending separate leads to a particular component from outside the housing, a coaxial-type cable could be used with the shield and axial wire separated and separately connected to a substrate conductor.

In FIG. 10, at the inner end 78 of the housing 76, there is a thermistor, infrared sensor or detector 122 oriented to face the tympanic membrane and to receive infrared radiation from the membrane, to be used in determining the temperature of the patient. This sensor would also fit in the apparatus of FIG. 2, apart from the pointing of the sources in FIG. 2 toward the tympanic membrane (as opposed to the ear canal lining). The sensor 122 can be conventionally adhered to the wall of the housing 76. In FIG. 10, two infrared sensor leads 120, for illustrative purposes, are shown leading from the sensor to the outside of the housing. The actual number, of course, may vary depending on the nature and characteristics of the sensor.

The sources, and sensor, for pulse oximetry may be operated in the visible light spectrum or in the near infrared.

Examples of sources (light-emitting diodes) and sensors of the type which may be used in accordance herewith are sources and/or sensors: found in Dialight Corporation's 597 Top View CBI Series Visible, 597 Top View Infrared Emitters Series, and 597 Top View Infrared Detectors Series; and found in Nonin Medical, Inc.'s Adult Flexi-Form Single Patient Use Sensor (Part No. 9000A), Neonatal Flexi-Form Single Patient Use Sensor (Part No. 9000N) and Pediatric Flexi-Form Single Patient Use Sensor (Part No. 9000T).

Figure 12:
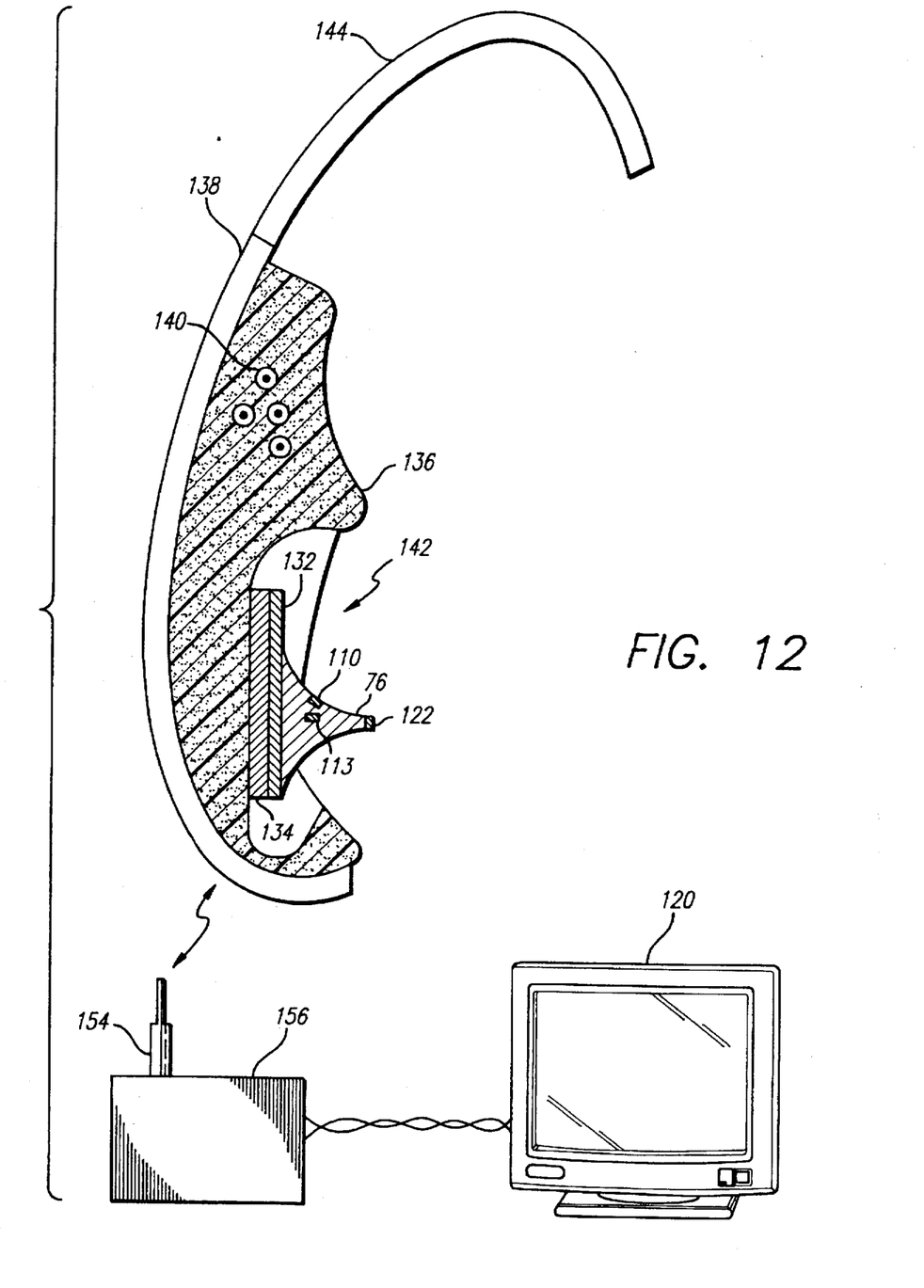
FIG. 12 is a cross sectional view of ear muff 138 which supports and positions integrated electronics package 142 in the auditory canal.

Referring now to FIG. 12, another embodiment of the present invention is shown in which communications between the transducers in housing 76 and the display and alarm devices in remote monitoring display 120 is accomplished by radio. In particular, radiation sources 110 and radiation detector 113 are mounted in housing 76 together with thermal detector 122 as described above. In addition, electronics controller 132 is affixed to the back of housing 76 and in turn supports transmitter package 134 forming integrated electronics package 142.

Integrated electronics package 142 is mounted within foam pad 136 of ear muff 138. Batteries 140 provide power for the components of integrated electronics package 142 and are conveniently positioned within foam pad 136 as shown. Ear muff 138 is supported on the patient's head by headband 144 for convenience.

Referring also to FIG. 13, transmitter package 134 includes transmitter 146, electromagnetic shield 148 and integrated antenna 150.

In operation, headband 144 is fitted to the head of the patient to be monitored so that ear muff 138 surrounds one ear which is cushioned by foam pad 136. Housing 76 fits into the auditory canal so that thermal detector 122 may determine body or core temperature from the tympanic membrane. Simultaneously, radiation sources 110 apply radiation to the ear canal for detection by radiation detector 113 to derive various pulse oximetry data. The thermal and pulse oximetry data is converted by electronics controller 132 to a serial bit stream in accordance with conventional techniques and applied to transmitter package 134.

Within transmitter package 134, the serial bit stream data is converted to radio frequency or r.f. signals by transmitter 146 and applied, via cable 152, to integrated antenna 150. Electromagnetic shield 148, through which cable 152 passes, is positioned between integrated antenna 150 and the patient to minimize the r.f. potential applied to the patient. Transmitter 146 may be operated at any convenient frequency for which it is designed, but preferably at a relative high frequency, in the range of about at least 2 gigahertz or greater so that the wavelength is extremely short. In this way, the physical length required for reasonable radiation efficiency for integrated antenna 150 is sufficiently short so that integrated antenna 150 may be positioned entirely within integrated electronics package 142.

The r.f. signals transmitted by integrated antenna 150 are picked up by base station antenna 154 at a remote station either within the patient's room or even at a remotely located monitoring station such as a central nursing station. The r.f. signal received by base station antenna 154 is processed by receiver/processor 156 which serves to convert the r.f. energy back to a representation of the thermal and pulse oximetry data such as a serial bit stream. The recovered data is then displayed on remote monitoring display 120.

It is understood that the present invention has been described by way of illustration and not limitation and that the scope of the invention is defined by the following claims.

What is claimed is:

1. An apparatus for monitoring multiple physiological variables of a patient, comprising:

an infrared (IR) temperature sensor for measuring temperature of the patient from a tympanic membrane at one end of an ear canal of the patient;

a pulse oximeter sensor for measuring oximetry data from a portion of a lining of the ear canal, said pulse oximeter sensor including:

first and second light sources and a light sensor for receiving light from said light sources, said light sources being adapted to be aimed away from said tympanic membrane to reduce thermal interference between said infrared temperature sensor and said light sensor;

said apparatus further including a communication circuit for outputting data produced by the pulse oximeter sensor and the infrared temperature sensor; and a housing for supporting said infrared temperature sensor, said pulse oximeter sensor, and said communication circuit, said light sources and said light sensor being angularly spaced from each other at an angle of about 90° or less.

2. The invention of claim 1, wherein said angle is between about 45° and about 90°.

3. The invention of claim 2, wherein said angle is about 60°.

4. The invention of claim 1, wherein the first and second light source and the infrared temperature sensor are activated in a time-division multiplex manner to reduce thermal interference by making the infrared temperature measurements while the light sources are off.

5. An apparatus for monitoring multiple physiological variables of a patient, comprising:

housing having an inner end, outer end and an elongated section between said ends, said housing being sized to fit in an ear canal of a patient;

a radiation source mounted along said elongated section to emit radiation toward a lining of the ear canal of the patient;

a first radiation sensor mounted along said elongated section, at an angle of about 90° or less with respect to said source, to receive radiation from said source following reflection by the lining of the ear canal at a reflection point;

a second radiation sensor mounted in said inner end to receive radiation, from a tympanic membrane of the patient in said ear canal, along a direction generally perpendicular to a plane including said radiation source, said first radiation sensor, and said reflection point.

6. The invention of claim 5, further including:

a second radiation source mounted along a first opening to emit radiation toward the lining of the ear canal of the patient.

7. The invention of claim 6, wherein:

said sources and said first sensor are pulse oximeter sources and a pulse oximeter sensor; and said second sensor is an infrared temperature sensor.

8. The invention of claim 5, wherein said apparatus further comprises:

a communication circuit coupled to said sensors for communicating signals responsive to said sensors; and an external processor for receiving said signals from said communication circuit and processing said signals into physiological data.

* * * * *